(12) United States Patent
Welp

(10) Patent No.: US 9,714,132 B2
(45) Date of Patent: Jul. 25, 2017

(54) MANUALLY OPERATED DISPENSER FOR MEDIA

(71) Applicant: MeadWestvaco Calmar GmbH, Hemer (DE)

(72) Inventor: Gisbert Welp, Sundern (DE)

(73) Assignee: WestRock Dispensing Systems Hemer GmbH, Norcross, GA (US)

( * ) Notice: Subject to any disclaimer, the term of this patent is extended or adjusted under 35 U.S.C. 154(b) by 72 days.

(21) Appl. No.: 14/651,534

(22) PCT Filed: Dec. 10, 2013

(86) PCT No.: PCT/EP2013/003727
§ 371 (c)(1),
(2) Date: Jun. 11, 2015

(87) PCT Pub. No.: WO2014/095004
PCT Pub. Date: Jun. 26, 2014

(65) Prior Publication Data
US 2015/0298893 A1    Oct. 22, 2015

(30) Foreign Application Priority Data
Dec. 20, 2012   (DE) .................. 10 2012 025 414

(51) Int. Cl.
*B65D 47/00* (2006.01)
*B67D 3/00* (2006.01)
(Continued)

(52) U.S. Cl.
CPC ......... *B65D 83/40* (2013.01); *A61M 15/0025* (2014.02); *A61M 15/08* (2013.01);
(Continued)

(58) Field of Classification Search
CPC .... A61M 15/0025; A61M 15/08; B65D 83/40
(Continued)

(56) References Cited

U.S. PATENT DOCUMENTS 2,737,416 A * 3/1956 Behr .................. B65D 83/40
215/228
5,105,993 A * 4/1992 La Haye ............ A61F 9/0008
210/321.89
(Continued)

FOREIGN PATENT DOCUMENTS

DE         8622273 U1    7/1989
DE         4400945 A1    7/1995
(Continued)

OTHER PUBLICATIONS

English translation of the International Preliminary Report on Patentability, dated Jul. 16, 2015, six pages.
(Continued)

*Primary Examiner* — Patrick M Buechner
*Assistant Examiner* — Jeremy W Carroll
(74) *Attorney, Agent, or Firm* — WestRock Intellectual Property Group

(57) ABSTRACT

Manually operated dispenser for media, with a reservoir (1), with a pump part (2) which is mounted on the reservoir (1) and comprises a nozzle-shaped discharge portion (3) with a discharge portion end (5) having a discharge opening (4), with an actuation mechanism (6) assigned to the pump part (2), and with a protective cap (7) covering at least the discharge portion end (5), wherein a soft porous insert (8) provided with an antimicrobial additive is inserted into the protective cap (7) and can be pressed when the protective cap (7) is fitted from above onto the discharge portion end (5) with spring support.

17 Claims, 4 Drawing Sheets

Figure 4:
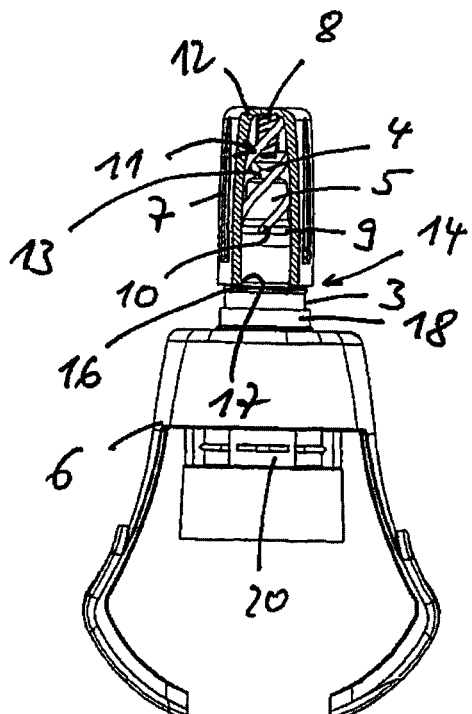

(51) Int. Cl.
*B65D 83/40* (2006.01)
*B05B 11/00* (2006.01)
*A61M 15/08* (2006.01)
*A61M 15/00* (2006.01)

(52) U.S. Cl.
CPC ...... *B05B 11/0005* (2013.01); *B05B 11/0008* (2013.01); *B05B 11/0032* (2013.01); *B05B 11/3056* (2013.01); *A61M 2205/0205* (2013.01); *A61M 2205/11* (2013.01); *B05B 11/0037* (2013.01)

(58) Field of Classification Search
USPC .................................. 222/562, 321.6, 321.8
See application file for complete search history.

(56) References Cited

U.S. PATENT DOCUMENTS

| | | | | |
|---|---|---|---|---|
| 5,433,343 A * | 7/1995 | Meshberg | ............. | A61M 15/08 222/154 |
| 5,516,006 A * | 5/1996 | Meshberg | ............. | A61M 15/08 222/162 |
| 6,000,580 A * | 12/1999 | Nilson | ............. | A61M 15/0025 220/367.1 |
| 7,854,352 B2 * | 12/2010 | Davies | ............. | B05B 11/0032 128/200.23 |
| 2002/0066752 A1 * | 6/2002 | Ritsche | ............. | B05B 11/0027 222/153.13 |
| 2005/0234402 A1 * | 10/2005 | Collins | ............. | A61M 15/009 604/151 |
| 2006/0180613 A1 * | 8/2006 | Manesis | ............. | A61F 9/0008 222/189.09 |
| 2008/0249459 A1 * | 10/2008 | Godfrey | ............. | A61M 15/009 604/19 |
| 2010/0108712 A1 * | 5/2010 | Manesis | ............. | A61F 9/0008 222/1 |
| 2010/0308082 A1 * | 12/2010 | Lamble | ............. | A61M 15/009 222/162 |

FOREIGN PATENT DOCUMENTS

| | | |
|---|---|---|
| DE | 10050982 A1 | 4/2002 |
| DE | 102008027598 A1 | 12/2009 |
| EP | 2363024 A3 | 3/2013 |
| WO | WO 92/04004 A1 | 3/1992 |
| WO | WO 01/83010 A1 | 11/2001 |

OTHER PUBLICATIONS

International Search Report corresponding to PCT/EP2013/003727 dated Mar. 25, 2014, three pages.

* cited by examiner

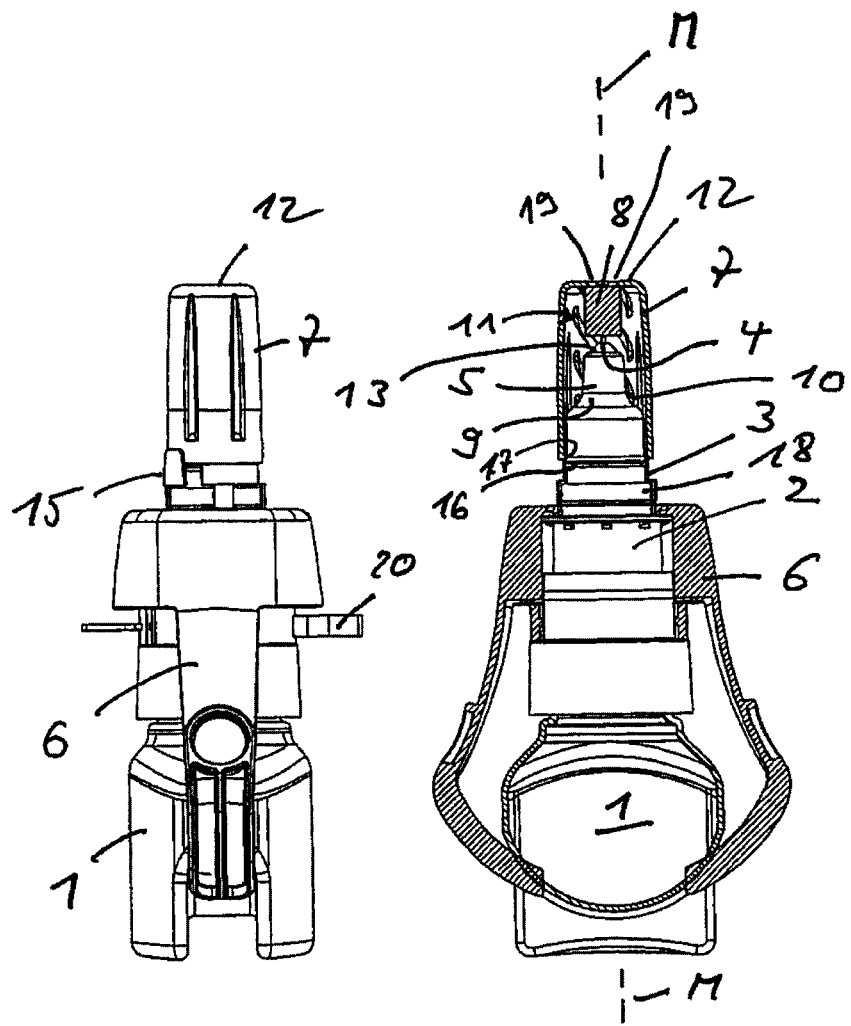

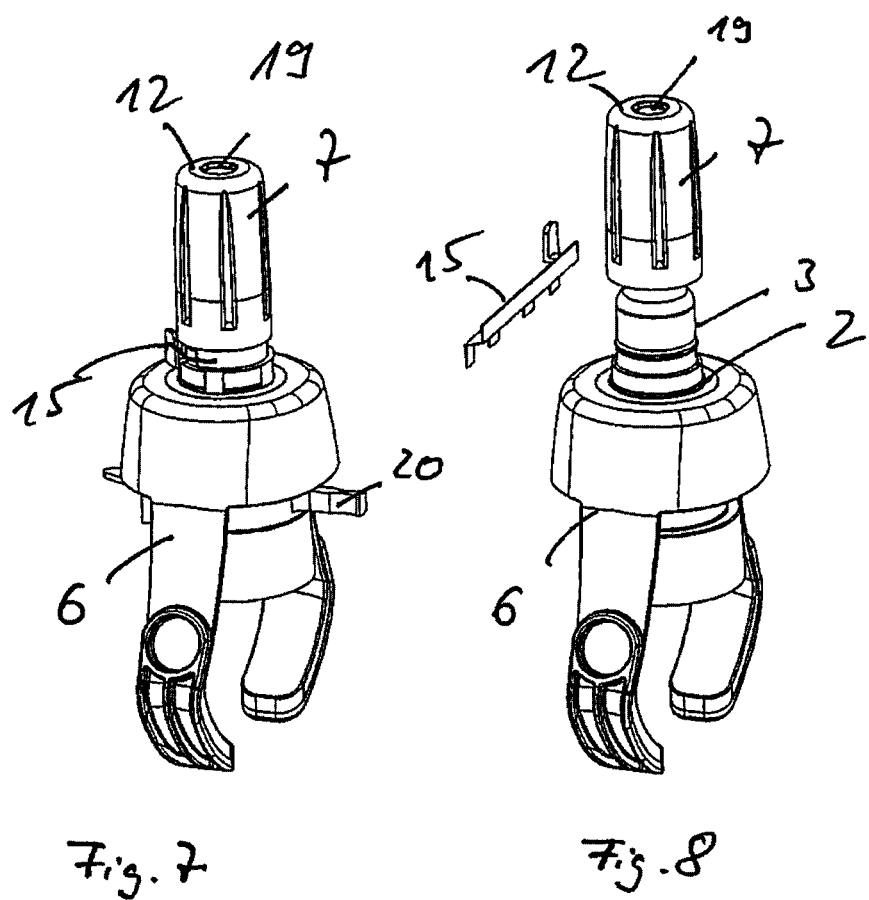

MANUALLY OPERATED DISPENSER FOR MEDIA

The invention relates to a manually operated dispenser for media in accordance with the preamble of Claim 1.

DE 44 00 945 A1 discloses a dispensing device of this kind for fluid media. A fluid pump container is composed of a cylindrical fluid container on which a pump part, having a dosing pump, is sealingly mounted by means of a sealing ring. The dosing pump is operated by an actuation element, which is held in its upper rest position by an elastic force. Between the upper rest position and the lower actuation position, the actuation element is movable along an actuation path. For actuation, the actuation element has a plate-shaped portion. The dosing pump conveys the fluid from the fluid container through a vertical fluid channel, which continues axially upwards through the actuation element as far as an outlet opening arranged at the tip of the actuation element. The tip of the actuation element can be closed by a closure cap. A disadvantage is that the closure cap can, as a result of use, become soiled on the inside by fluid residues.

DE 100 50 982 A1 discloses a dispenser, in particular an atomizer for flowable substances, in particular pharmaceuticals, which dispenser uses a pump that has to be operated one or more times for priming. Its discharge nozzle is covered by a protective cap, which is suitable for collecting and storing the medium that is released during the priming strokes and before the start of the actual useful strokes. The protective cap is secured on the dispenser during the priming strokes. The protective cap is able to take up the amount of media that is sprayed, injected or dropped into it, e.g. in a sponge-like element. The protective cap is then removed for the actual actuation stroke. A storage space is formed in the protective cap since the latter, especially in its upper area, is at a greater distance from the nose adapter. In this storage space, a foam-like or sponge-like element is provided as storage means, which element is arranged in a ring shape surrounding the nose adapter. The storage space, which takes up the medium released during priming strokes, can be vented to the outside. The protective cap is used here as an intermediate storage for liquid medium in order to improve the dosing accuracy. The actual purpose of use of the protective cap, that of covering and protecting the discharge opening, is lost here, since the protective cap becomes a spray shield.

A fluid-dispensing device with a protective end cap is known from U.S. Pat. No. 7,854,352 B2. A resilient insert serving as a stopper can be inserted into the protective cap.

U.S. Pat. No. 6,000,580 A discloses a dispensing device for dispensing a liquid, sterile, preservative-free preparation, in which device no bacterial growth occurs. This dispensing device comprises a dispensing part and a protective cap for the dispensing part. The protective cap is provided with at least one opening, which allows free access of air to the dispensing part. The cap can be provided with absorbent materials which touch the dispensing outlet of the dispensing part. At least some parts of the absorbent materials are in contact with the ambient air.

US 2010/0108712 A1 discloses a dispenser with a protective cap. The cap can be lined with an anti-microbial material that prevents contamination of the discharge nozzle. The liner is preferably composed of an elastic material, such as rubber, or a sponge. The antimicrobial substance can be introduced in the elastic material or as a coating.

U.S. Pat. No. 5,105,993 A1 discloses a dispenser with a cap into which an antibacterial insert is introduced.

An object of the invention is therefore to make available a manually operated dispenser for media, in which the protective function of the protective cap for the discharge opening is improved.

This object is achieved by the features of Claim 1.

A manually operated dispenser for media is thereby made available in which a protective cap, when fitted onto the dispenser, wipes the discharge portion end having the discharge opening. A soft porous insert absorbs media residues that have been left on the discharge portion end of the dispenser after use thereof. The fact that the insert is provided with an antimicrobial additive permits the use of bactericidal, germicidal, virucidal and/or fungicidal means. The fitting of the protective cap thus has an antiseptic action on the discharge opening. This prevents germs from forming in the area of the discharge opening.

The insert is preferably produced by being impregnated, finished or mixed with the antimicrobial additive. Known composite foams having an antimicrobial finish or action can be used. This applies in the same way to other soft porous inserts, such as a membrane, nonwoven, or other textile materials from natural or synthetic fibres, which can also be actively impregnated.

A torsion spring which is provided by preference ensures a sufficient pressure force, which acts as a cleaning force. The torque introduced together with the pressure force follows the procedure typical for wiping movements, for example a rubbing movement. According to the invention, the soft and porous insert is used not only as a way of taking up medium, but also as a wiping device. The removal of residues of media can be used for cleaning purposes and also for analysis purposes.

By way of the spring support, preferably using a torsion spring, in combination with a snap-fit connection provided for securing the protective cap on the discharge portion end, a forced movement for wiping the discharge portion end can be triggered when the protective cap is placed onto the dispenser. This forced movement can be triggered via a resilient length of the torsion movement that goes beyond the transition of the locking elements of the snap-fit connection. The manual pressure force needed for the snapping-in of the snap-fit connection then leads to an overshoot of the transition at which the protective cap with its insert is pressed against the discharge portion end and, as a result of the introduced torque, rubs across the discharge portion end.

Media residues, in particular liquid media residues, from previous dispensing procedures can thus be removed from the discharge opening when the protective cap is fitted. Drying off of the insert can be improved if the protective cap has vents, preferably in that area of the protective cap surrounding the insert.

Further embodiments of the invention are set forth in the following description and in the dependent claims.

The invention is explained in more detail below on the basis of the illustrative embodiments shown in the attached figures.

Figure 6:
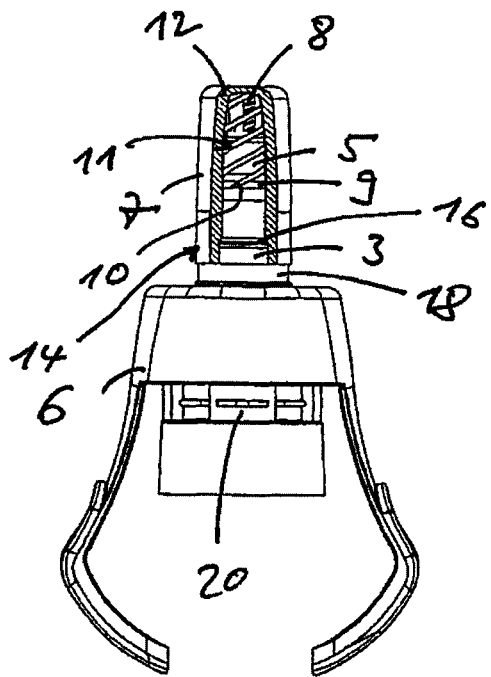
Figure 3:
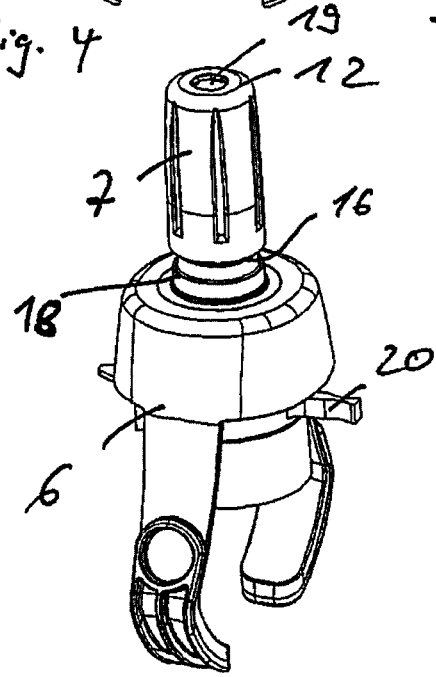
Figure 5:
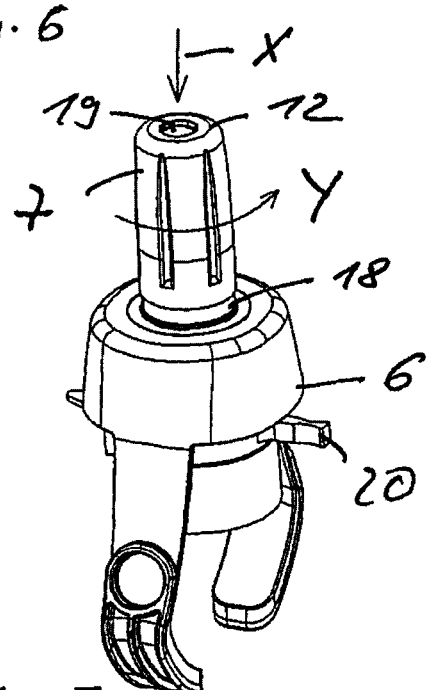
Figure 9:
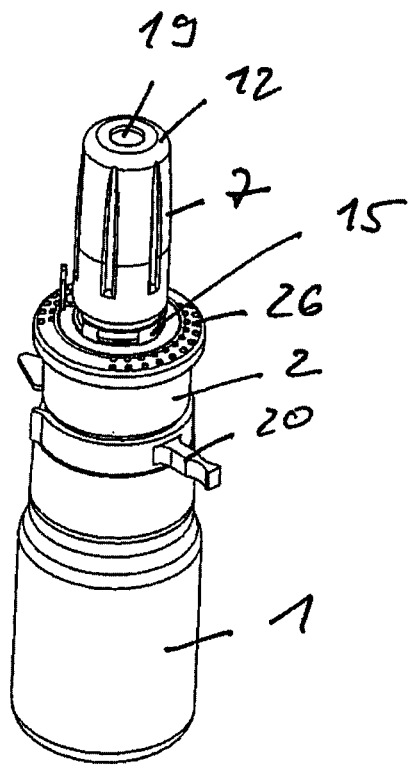
Figure 10:
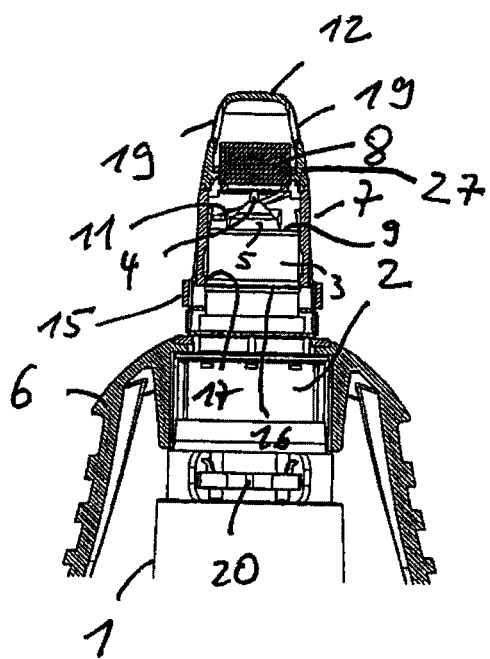
Figure 11:
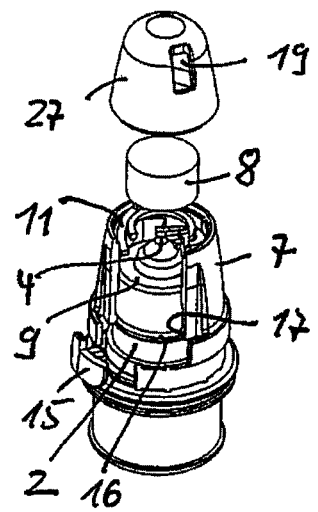

FIG. 1 shows a schematic side view of a manually operated dispenser according to a first illustrative embodiment, FIG. 2 shows a schematic cross section of FIG. 1, FIG. 3 shows a schematic perspective view of a partial area of the dispenser, with a protective cap fitted and after removal of a tear-off ring, FIG. 4 shows a schematic cross section of FIG. 3, FIG. 5 shows a schematic perspective view of a partial area of the dispenser with the protective cap pressed on, FIG. 6 shows a schematic cross section of FIG. 5, FIG. 7 and FIG. 8 show schematic perspective views of a partial area of the dispenser before and after the removal of a tear-off strip for a first use of the dispenser, FIG. 9 shows a schematic perspective view of a manually operated dispenser according to a second illustrative embodiment, FIG. 10 and FIG. 11 show a schematic cross section and a perspective and partially exploded view of a manually operated dispenser according to a third illustrative embodiment.

The invention relates to a manually operated dispenser for media, which dispenser is provided in particular for discharging a liquid medium, an aerosol or other fluid medium, if appropriate with solid fractions. The media are, for example, pharmaceuticals.

As FIG. 1 and FIG. 2 show, the dispenser comprises a reservoir 1 and pump part 2 mounted on the reservoir 1. The pump part 2 is movable relative to the reservoir 1 in a stroke direction, preferably between an upper rest position and a lower actuation position. The stroke direction has an axial orientation here.

The pump part 2 can be configured in a known manner, for example as described in DE 10 2008 027 598 A1.

As FIG. 2 shows, the pump part 2 comprises a nozzle-shaped discharge portion 3, with a discharge portion end 5 having a discharge opening 4. The pump part 2 is assigned an actuation mechanism 6, in order to discharge the medium by manual actuation of the actuation mechanism 6. For this purpose, the medium is stored in the reservoir 1, from which the medium is discharged by means of the pump part 2 through a media channel in the discharge portion 3 via individual pump strokes. The nozzle-shaped discharge portion 3 can have a different design, if appropriate also an ergonomic design, depending on the intended use, for example as nasal adapter or drop adapter. The pump part 2 and the reservoir 1 are here arranged coaxially.

For at least the discharge portion end 5, a covering protective cap 7 is provided, which is intended to protect the discharge opening 4, and the discharge portion end 5 surrounding the latter, when the dispenser is not in use. This is intended to avoid the dispenser being soiled and/or damaged in the area of the discharge of the medium.

The protective cap 7 is a preferably bushing-shaped lid which covers at least the discharge portion end 5 and which can repeatedly be firmly fitted in place after use of the dispenser.

As FIG. 2 to FIG. 5 show, a soft porous insert 8 provided with an antimicrobial additive is inserted into the protective cap 7 and can be pressed when the protective cap 7 is fitted from above onto the discharge portion end 5 in a spring supported way.

The insert 8 can be produced by being impregnated, finished or mixed with the antimicrobial additive. Known composite foams having an antimicrobial finish or action can be used. This applies in the same way to other soft porous inserts, such as a membrane, nonwoven, or other textile materials from natural or synthetic fibres, which can also be actively impregnated. For example, reference is made in this connection to the antimicrobially finished sponges known from EP 2 363 024 A2.

The discharge portion 3 forms a stand surface 9 for a free end 10 of a torsion spring 11 which is clamped in the protective cap 7 preferably for spring support. The loading of the torsion spring 11, when the protective cap 7 is pressed onto the discharge portion end 5, introduces a torque that turns the protective cap 7 relative to the discharge portion 3. FIG. 5 illustrates the directions of the movement components by the arrows X and Y. The torsion spring 11 is loaded by the ends being pressed together. When loaded, the protective cap 7 turns about its longitudinal axis. The pivoting movement in the direction of the arrow Y about a rotation axis then preferably takes place about a centre axis M (cf. FIG. 2) of the pump part 2 and/or of the dispenser. The rotation angle is dependent on the length, preferably a number of windings or a torsion bar length, and diameter of the torsion spring and on the strength of the spring material used. Longer torsion springs 11 provide a greater rotation angle. A small rotation angle is generally sufficient, which can measure 0.5 to 3 mm, for example.

As FIG. 2 and FIG. 4 show, the interior of the protective cap 7 is equipped, adjacent to a protective cap wall 12 at the head end, with the soft porous insert 8, which is preferably designed like a cushion. The insert 8 then preferably has an axial extent into the interior of the protective cap 7, as a result of which the insert 8 yields and takes up fluid in the axial direction. The soft porous insert 8 can be designed as a sponge, membrane, nonwoven or other textile material from natural and/or synthetic fibres. For example, a PU foam, which has good absorbency, is particularly suitable as a sponge.

It is essential that the insert 8 takes up fluid when it is pressed against the discharge portion end 5 when the protective cap 7 is pressed on. If the insert 8 extends from the protective cap wall 12 at the head end into the interior of the protective cap 7 by an axial length, the insert 8 is pressed onto a head wall 13 of the discharge portion end 5 when the protective cap 7 is fitted in place and pressed on. The discharge opening 4 is arranged in the head wall 13. The insert 8 preferably has a radial extent that is greater than the diameter of the discharge opening 4, as is shown in FIG. 4. When pressed on, the insert 8 thus comes into contact with an area formed by the head wall 13 around the edge area of the discharge opening 4. Media residues left around the discharge opening 4 during a discharge stroke or spray procedure can thus be caught by the insert 8 and taken up. According to the invention, this pressing-on of the insert 8 in order to take up media residues from the discharge portion end 5 in the arrow direction X (cf. FIG. 5) is combined with a movement component in arrow direction Y, in order to generate as it were a rubbing and wiping movement, as a result of which the fluid uptake is improved.

The torsion spring 11 provided for this purpose is, for example, a torsion bar spring, helical spring or rubber spring. The torsion spring 11 is bar-shaped with a preferably axially directed resilient length in the interior of the protective cap 7. The insert 8 is preferably surrounded by the torsion spring 11. The insert 8 and the torsion spring 11 are then stressed jointly when the protective cap 7 is pressed on. The torsion spring 11 is therefore an elastic bar, of which one end is clamped on the protective cap 7, and a torque is introduced at the free end 10 thereof under a load. The effect of this is that the free end 10 turns at least about a small angle relative to the clamped end and therefore the loose protective cap 7, under an applied manual pressure force in arrow direction X, turns relative to the discharge portion 3 in arrow direction Y.

To accommodate the insert 8 and the torsion spring 11 in the interior of the protective cap 7, the protective cap 7 preferably has an excess length in relation to at least the discharge portion end 5 that is to be covered. When the protective cap 7 is fitted, preferably securely, in the state when the dispenser is not in use, the insert 8 and the torsion spring 11 are then unloaded or at least partially unloaded.

As is also shown in FIG. 3 to FIG. 6, the protective cap 7 can preferably be secured removably on the discharge portion 3 via a snap-fit connection 14. FIG. 4 shows the snap-fit elements of this snap-fit connection 14 before a first use and in an as yet unlocked state. Before the first use, a tear-off ring 15 is provided between the protective cap 7 and the actuation mechanism 6, in order to indicate a first use. FIG. 7 and FIG. 8 show the removal of the tear-off ring 15 for the first use. It is only after the tear-off ring 15 has been detached that the protective cap 7 can be removed and the pump part 2 can be operated in order to discharge medium.

As FIG. 4 shows, the snap-fit connection 14, as a segmented ring snap-fit connection on the discharge portion 3, comprises an outer bead 16 which is far from the end and is arranged as a shaped part. The protective cap 7 can lock releasably on the outer bead 16 like a lid via segmented inner ring snap-fit elements 17 near the end. Before the first use, shown in FIG. 4, there is no join between the outer bead 16 and the inner ring snap-fit elements 17, since the inner ring snap-fit elements 17 lie above the outer bead 16. Before a first use, there is no need for media residues to be wiped off.

As FIG. 6 shows by comparison with FIG. 5, the torsion spring 11 preferably has a resilient length that goes beyond the transition of the locking elements of the snap-fit connection 14 as defined by the outer bead 16 of the snap-fit connection 14. The resilient length of the torsion spring 11 is defined by a stop 18, which limits an overshoot path of the protective cap 7 relative to a snap-fit element, here the outer bead 16, on the discharge portion 3. When a manual force is applied to press the protective cap 7 into the snap-fit connection 14, an as it were forced overrun of the protective cap 7 as far as the stop 18 is generated. The torsion spring 11 also acts as a damping member, such that the generated rotation movement of the spring element leaves behind an elastic impression. The stop 18 can be formed separately from the discharge portion 3, since it need only be assigned to the latter. FIG. 5 shows the protective cap 7 in abutment against the stop 18. When the protective cap 7 is unloaded, it moves upwards until the inner ring snap-fit elements 17 engage behind the outer bead 16 as releasable join position (not shown). The torsion spring 11 holds the join position of the snap-fit connection 14 preferably under spring pretensioning.

The protective cap 7 can have one or more openings 19, in the area where the insert 8 is enclosed, in order to form an air-permeable closure. Here, the one or more openings 19 are arranged in the protective cap wall 12, for example. The protective cap 7 can thus be better ventilated for drying off the soft porous insert 8 during the time when the dispenser is not in use.

Examples of materials that can be used for the torsion spring 11 are polypropylene (PP), polyoxymethylene (POM) or polybutylene terephthalate (PBT). The covering length of the protective cap 7 relative to the discharge portion 3 can be chosen depending on the particular use. In the case of a nasal adapter, for example, a longer protective cap for coverage is provided than in the case of a drop adapter. In a known manner, an insertable actuation blocker 20 for the pump part 2 can be provided.

The soft porous insert 8 can also be a rod-shaped carrier, which can be exchangeable as a collector for filter purposes or analysis purposes, such as DNA determination.

FIG. 9 shows a second illustrative embodiment of a manually operated dispenser, which differs from the above-described illustrative embodiment in that another actuation mechanism 26 is provided for the pump part 2. The actuation mechanism 26 is designed here in a known manner as a handle plate. Otherwise, the above comments accordingly apply. The design of the protective cap 7 is independent of the nature and direction of the engaging actuation mechanism.

FIG. 10 and FIG. 11 show a third illustrative embodiment of a manually operated dispenser, which differs from the above-described first illustrative embodiment in that the protective cap 7 has a head portion 27 that can be applied releasably. This is advantageous especially if the insert 8 is frequently exchanged or is used as a collector for analysis purposes. It can then be the case that the insert 8 is exchanged after just one or a few pump strokes. The torsion spring 11 is then preferably short, for example 5 to 10 mm and/or only two to three windings, with the result that only a slight pivoting movement about the rotation axis occurs when the torsion spring 11 is loaded. This can be at least partially compensated by a voluminous insert 8 which, if elastic material is used on account of its compression behaviour, can combine an axial movement with pivoting movements. The absorbing and wiping effect thus obtained is good enough to take up media from the discharge opening 4 into the insert 8. For this purpose, the insert 8 can be a shaped insert which, for example, is shaped like a plug or a portion of a plug.

According to an illustrative embodiment not shown, it is possible, as an alternative to the torsion spring 11, to use a spring element that can be loaded by a pressure force, for example a flexible spring or compression spring.

The invention claimed is:

1. Manually operated dispenser for media, with a reservoir, with a pump part which is mounted on the reservoir and comprises a nozzle-shaped discharge portion with a discharge portion end having a discharge opening, with an actuation mechanism assigned to the pump part, and with a protective cap covering at least the discharge portion end, wherein a soft porous insert provided with an antimicrobial additive is inserted into the protective cap and can be pressed when the protective cap is fitted from above onto the discharge portion end with a spring, wherein the insert is surrounded by the spring.

2. Manually operated dispenser according to claim 1, wherein the insert is impregnated, finished or mixed with the antimicrobial additive.

3. Manually operated dispenser according to claim 1, wherein the discharge portion forms a stand surface for a free end of the spring, which is clamped in the protective cap and whose loading introduces a torque that turns the protective cap relative to the discharge portion.

4. Manually operated dispenser according to claim 3, wherein the spring is a torsion bar spring, helical spring or rubber spring.

5. Manually operated dispenser according to claim 1, wherein the soft porous insert is designed as sponge, membrane, nonwoven or other textile material from natural and/or synthetic fibers.

6. Manually operated dispenser according to claim 1, wherein the soft porous insert is a cushion.

7. Manually operated dispenser according to claim 1, wherein the protective cap can be secured removably on the discharge portion by a snap-fit connection.

8. Manually operated dispenser according to claim 7, wherein the protective cap has openings, in the area where the insert is enclosed, in order to form an air-permeable closure.

9. Manually operated dispenser according to claim 1, wherein the protective cap has a head portion that can be applied releasably.

10. A manually operated dispenser, comprising:
a reservoir;
a pump mounted on the reservoir, the pump comprising:
   a discharge portion;
   a discharge opening in the discharge portion; and
   an actuation mechanism;
a cap;
a torsion spring positioned in the cap;
a porous insert positioned in the cap and surrounded by the torsion spring; and
an antimicrobial additive in the porous insert.

11. The manually operated dispenser of claim 10, wherein the antimicrobial additive is impregnated in the porous insert.

12. The manually operated dispenser of claim 10, wherein the torsion spring is selected from the group consisting of a torsion bar spring, a helical spring, and a rubber spring.

13. The manually operated dispenser of claim 10, wherein the insert further comprises an insert selected from the group consisting of a sponge, a membrane, a cushion, a nonwoven textile material, and a woven textile material.

14. The manually operated dispenser of claim 13, wherein the insert further comprises natural fibers.

15. The manually operated dispenser of claim 13, wherein the insert further comprises synthetic fibers.

16. The manually operated dispenser of claim 10, wherein the cap is removeably secured to the pump.

17. The manually operated dispenser of claim 10, wherein the cap further comprises at least one opening adjacent the position of the insert in the cap.

\* \* \* \* \*